July 6, 1948. E. S. BOERNER Plant Pat. 799
ROSE PLANT
Filed Dec. 5, 1946
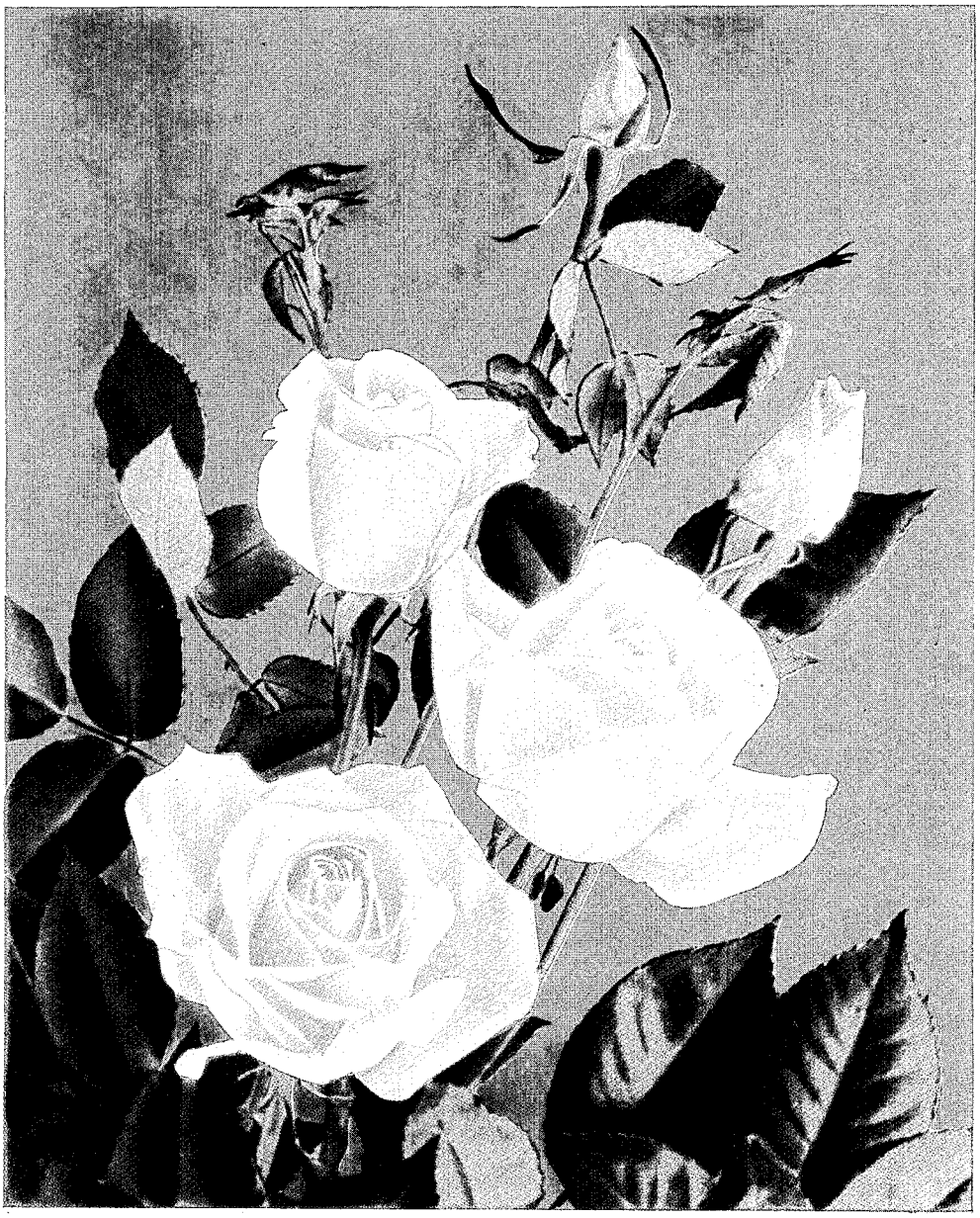
Inventor:
E. S. Boerner
By: Robb & Robb
Attorneys Patented July 6, 1948

Plant Pat. 799

UNITED STATES PATENT OFFICE

799

ROSE PLANT

Eugene S. Boerner, Newark, N. Y., assignor to Jackson & Perkins Company, Newark, N. Y., a corporation of New York Application December 5, 1946, Serial No. 714,268

1 Claim. (Cl. 47—61)

The present discovery relates to a new and distinct variety of Rose plant, originating as a sport of the well-known variety "Briarcliff" which is notable as one of the standards in greenhouse and garden.

This new variety differs from other Hybrid Teas in that it produces a very uniform type of flower with a different light shade of color. In color, it is lighter than that of the parent variety, but of greater importance, it does not have the extreme variations in color in a given number of plants, as found to be the case in reference to its parent. The value of uniform buds for greenhouse cutting is too well known to be discussed other than to say that such characteristic eliminates much grading and extra handling on the part of a grower.

One of the valuable features of this new variety is the clarity and constancy of the color gradation in the half open and open flower, as clearly indicated in the accompanying illustration, said color gradation running from a uniform light shade of pink (Thulite), to Cameo Pink, with a suffusion of Primrose Yellow.

The complete suffusion of yellow in all stages of the development, starting with the Light Jasper Red of the bud stage and carrying through to the final Cameo Pink of the full-open stage, distinguishes this variety from its parent and gives to the flower a warm glow with no indication of the objectionable blue shade in any of the stages.

In the drawings is shown a number of specimens of this new rose in different stages from bud to full blown, including foliage likewise in the various stages of development.

Asexual reproduction of this new variety shows the foregoing characteristics come true to form and are established.

The following is a detailed description of this new variety, the color terminology being in accordance with Ridgway's Color Standard:

Parentage: Sport. Parent variety—"Briarcliff."

Classification: Botanic and commercial—hybrid tea.

*Flower*

(Observations made in greenhouses at Newark, New York, in the month of February, 1946.)

Blooming habit: Recurrent—continuous.

Bud:

*Size.*—Large.

*Form.*—Pointed. Is not affected by wet or hot weather.

*Color.*—When sepals first divide—Light Jasper Red, Plate 13; when petals begin to unfurl—Spinel Pink, Plate 26; when half blown—inside of petals, Thulite Pink, Plate 26, overcast with Pale Yellow Orange, Plate 3; reverse of petals, Rosolane Pink, Plate 26, overcast with Pale Yellow Orange, Plate 3.

*Sepals.*—Branched, "hood" above bud. Curl back when petals begin to unfurl. *Color.*—inside—Kildare Green, Plate 31; outside—Cerro Green, Plate 5.

*Calyx.*—Shape—funnel. Size—large. Aspect—smooth. Odor when rubbed—none. Color—Lettuce Green, Plate 5.

*Peduncle.*—Length—long. Aspect—smooth. Color—Lettuce Green, Plate 5. Strength—stiff; heavy.

*Opening.*—Opens up well; is not affected by adverse weather conditions.

Bloom:

*Size.*—Large. Average size when fully expanded, 5 inches.

*Borne.*—Singly.

*Stems.*—Long; strong.

*Form.*—When first open—high center. Permanence—retains its form to the end.

*Petalage.*—Double (full but open center). Number of petals under normal conditions, 30 to 35.

*Color.*—Center of flower—Deep Rose Pink, Plate 12. Outer petals—Rose Pink, Plate 12. Base of petals (aiglet)—Citron Yellow, Plate 16. Inside of petals—Thulite Pink, Plate 26, lightening to Cameo Pink, Plate 26, diffused with Primrose Yellow, Plate 30. Reverse of petals—Rose Pink, Plate 12, lightening to Cameo Pink, Plate 26, suffused with Primrose Yellow, Plate 30. General tonality from a distance—Thulite Pink, Plate 26, overcast with Primrose Yellow, Plate 30.

*Discoloration.*—General tonality at end of first day—Thulite Pink, to Cameo Pink, Plate 26, overcast with Primrose Yellow, Plate 30. Second day—Rose Pink, Plate 12, to Cameo Pink, Plate 26, overcast with Primrose Yellow, Plate 30. Third day—Cameo Pink, Plate 26, overcast with Primrose Yellow, Plate 30.

Petals:

*Texture.*—Leathery; it not affected by hot or wet weather.

*Appearance.*—Inside — satiny; outside—shiny.

*Form.*—Oval.

*Arrangement.*—Imbricated (regularly arranged shinglelike). Petaloids in center—few; small.

*Persistence.*—Drop off cleanly.

*Fragrance.*—Strong. Nature—"Old Rose" perfume (centifolia).

*Lasting quality.*—On the plant and as cut flower—long.

Genital organs:

*Stamens, anthers.*—Large; many. Color—Light Cadmium, Plate 4. Arrangement—regular around styles.

*Stamens, filaments (threads).*—Long. Color—Pinard Yellow, Plate 4.

*Pollen.*—Buff Yellow, Plate 4.

*Styles.*—Bunched; uneven length; medium length; heavy.

*Stigmas.*—Picric Yellow, Plate 4.

*Ovaries.*—All enclosed in calyx.

*Plant*

Form: Bush.

Growth: Very vigorous; upright.

Foliage: 3–5 leaflets.

*Size.*—Large.

*Quantity.*—Abundant.

*Color.*—New foliage: upper side—Oxblood Red, Plate 1, mid-rib, Oil Green, Plate 5; under side—Oxblood Red, Plate 1. Old foliage: upper side—Cress Green, Plate 31; serrations, Oxblood Red, Plate 1; under side—Light Hellebore Green, Plate 17; serrations, Oxblood Red, Plate 1.

*Shape*—Oval pointed.

*Texture.*—Upper side—leathery; under side—smooth. Ribs and veins—prominent.

*Edge.*—Serrated (saw toothed).

*Serrations.*—Single; large.

*Leaf stem.*—Chrysolite Green, Plate 31. Under side—smooth.

*Stipules.*—Long; smooth.

*Disease resistance.*—Good.

Wood:

*New Wood.*—Buffy Citrine, Plate 16. Bark—smooth.

*Old Wood.*—Light Cress Green, Plate 31. Bark—Smooth.

Thorns:

*Thorns.*—Quantity on main stalks from base and on laterals from stalk—few. Form—narrow base; medium length; hooked downward. Color when young—Eugenia Red, Plate 13. Position—irregular.

*Prickles.*—Quantity on main stalks and on laterals—none.

*Short needles.*—Quantity on main stalks and on laterals—none.

I claim:

A new and distinct variety of Rose plant, characterized as to novelty by the uniformity of the flowers throughout any given number of plants, both as to type and color, the lightness of this color imparted to the flowers by their characteristic suffusion of yellow, and the clarity and constancy of the pink coloring gradation, with this suffusion, running throughout the development from bud stage to full-open stage, with absence of blue shade in any of the stages, substantially as shown and described.

EUGENE S. BOERNER.